US012582326B2

(12) United States Patent
Swanström et al.

(10) Patent No.: US 12,582,326 B2
(45) Date of Patent: Mar. 24, 2026

(54) METHOD AND SYSTEM FOR AUTOMATICALLY DETECTING A CLINICALLY RELEVANT LEAK

(71) Applicant: QAELON MEDICAL, Strasbourg (FR)

(72) Inventors: Lee Swanström, Cabris (FR); Michele Diana, Saverne (FR); Bruno Mutet, Haguenau (FR); Eran Shlomowitz, North York (CA)

(73) Assignee: QAELON MEDICAL, Strasbourg (FR)

( * ) Notice: Subject to any disclaimer, the term of this patent is extended or adjusted under 35 U.S.C. 154(b) by 760 days.

(21) Appl. No.: 17/785,304

(22) PCT Filed: Dec. 17, 2020

(86) PCT No.: PCT/EP2020/086810
§ 371 (c)(1),
(2) Date: Jun. 14, 2022

(87) PCT Pub. No.: WO2021/123012
PCT Pub. Date: Jun. 24, 2021

(65) Prior Publication Data
US 2023/0013722 A1     Jan. 19, 2023

(30) Foreign Application Priority Data

Dec. 18, 2019    (EP) ..................................... 19315163

(51) Int. Cl.
*A61B 5/00* (2006.01)
*A61B 5/03* (2006.01)
*A61B 17/11* (2006.01)

(52) U.S. Cl.
CPC ............ *A61B 5/036* (2013.01); *A61B 5/4255* (2013.01); *A61B 17/11* (2013.01)

(58) Field of Classification Search
CPC ....... A61B 5/036; A61B 5/4255; A61B 17/11; A61B 2505/05; A61B 5/4842;
(Continued)

(56) References Cited

U.S. PATENT DOCUMENTS 5,399,159 A * 3/1995 Chin ................... A61M 13/003
604/26
9,733,147 B2 * 8/2017 Decker ................. G01M 3/007
(Continued)

FOREIGN PATENT DOCUMENTS

WO        2020021520 A1     1/2020

OTHER PUBLICATIONS

International Search Report mailed on Apr. 8, 2021, in corresponding International Application No. PCT/EP2020/086810, 6 pages.
(Continued)

*Primary Examiner* — May A Abouelela
(74) *Attorney, Agent, or Firm* — Maier & Maier, PLLC

(57)        ABSTRACT

A method for automatically detecting a clinically relevant leak and/or inadequate closure following a medical procedure, in a hollow organ residing in the interior volume of a body cavity. The test method includes the steps of: injecting, via an adapted injection element, a specific test gas or a gas mixture containing at least one test gas, into the organ, analyzing the gas mixture and measuring the test gas concentration in the interior volume of the body cavity via an adapted detection element and at least during a measurement window, evaluating the likelihood of the presence of a leak and its degree of severity, by comparing stored data and real-time data with each other. The pressure difference between the interior of the hollow organ(s) and the interior volume of the body cavity is controlled or mastered at least at a given moment during at least one measurement window.

19 Claims, 10 Drawing Sheets

(58) Field of Classification Search
CPC ...... A61M 2202/0283; A61M 2205/15; A61M
2205/3344; A61M 13/003; A61M
2205/502; A61M 2205/70
See application file for complete search history.

(56) References Cited

U.S. PATENT DOCUMENTS

| | | | | |
|---|---|---|---|---|
| 9,841,342 | B2 * | 12/2017 | Walter | G01M 3/202 |
| 10,408,763 | B2 * | 9/2019 | Gamache | G01N 21/73 |
| 10,928,268 | B2 * | 2/2021 | McNeil | G01N 25/4873 |
| 2006/0249150 | A1 * | 11/2006 | Dietz | A61M 16/022 128/204.23 |
| 2007/0157704 | A1 | 7/2007 | Jenneus et al. | |
| 2007/0163604 | A1 | 7/2007 | Mikkaichi et al. | |
| 2009/0173144 | A1 | 7/2009 | Lukens | |
| 2011/0071367 | A1 * | 3/2011 | Court | A61M 1/3656 600/300 |
| 2011/0259330 | A1 * | 10/2011 | Jafari | A61M 16/024 702/51 |
| 2013/0118496 | A1 * | 5/2013 | Truschel | A61M 16/06 702/45 |
| 2013/0197471 | A1 * | 8/2013 | Williams | A61M 5/365 604/247 |
| 2013/0317765 | A1 * | 11/2013 | Rao | A61M 16/026 702/51 |
| 2014/0199193 | A1 * | 7/2014 | Wilt | A61M 1/341 417/474 |
| 2014/0200437 | A1 * | 7/2014 | Yager | A61B 5/72 600/420 |
| 2014/0216451 | A1 * | 8/2014 | Jaffe | A61M 16/021 128/202.22 |
| 2015/0017682 | A1 * | 1/2015 | Adam | A61B 17/1114 600/581 |
| 2015/0105701 | A1 * | 4/2015 | Mayer | A61N 7/02 601/3 |
| 2015/0198501 | A1 * | 7/2015 | Rule | A61M 5/16854 73/40.5 R |
| 2015/0272499 | A1 * | 10/2015 | Shlomovitz | A61B 5/14503 600/560 |
| 2016/0082173 | A1 * | 3/2016 | Coll | A61M 1/155 604/114 |
| 2016/0101227 | A1 * | 4/2016 | Norris | A61M 1/155 604/29 |
| 2016/0325056 | A1 * | 11/2016 | Hiraga | A61B 17/3474 |
| 2018/0028769 | A1 * | 2/2018 | Obenchain | A61M 16/0051 |
| 2018/0117271 | A1 * | 5/2018 | Wigforss | G16H 20/40 |
| 2018/0133446 | A1 * | 5/2018 | Shikhman | A61M 31/002 |
| 2018/0264181 | A1 * | 9/2018 | Gregory | A61M 1/73 |
| 2019/0183381 | A1 * | 6/2019 | Frushour | G09B 23/28 |
| 2019/0247680 | A1 * | 8/2019 | Mayer | A61B 17/32 |
| 2019/0316948 | A1 * | 10/2019 | Karol | A61M 1/159 |
| 2019/0358372 | A1 * | 11/2019 | Askem | A61M 1/98 |
| 2021/0138140 | A1 * | 5/2021 | Plahey | A61M 1/1565 |
| 2021/0187175 | A1 * | 6/2021 | Quintanar | A61M 1/913 |
| 2021/0308390 | A1 * | 10/2021 | O'Dea | A61M 13/003 |

OTHER PUBLICATIONS

Written Opinion of the International Searching Authority mailed on Apr. 8, 2021, in corresponding International Application No. PCT/EP2020/086810, 19 pages.

\* cited by examiner

METHOD AND SYSTEM FOR AUTOMATICALLY DETECTING A CLINICALLY RELEVANT LEAK

FIELD

The present invention relates to the field of medical procedures, methods, systems and devices, more specifically minimally invasive surgical procedures and diagnostic systems to evaluate the integrity of an organ located in a body cavity, in particular of a tubular or hollow organ, as well as the size of a perforation or of an incomplete closure during the course of a surgical procedure.

BACKGROUND

In this context, the invention concerns more precisely an improved reliable system, and a corresponding method, for detecting leaks and/or verifying adequate closure following a medical procedure. Most preferably, the invention concerns a method and a system for detecting luminal leaks and/or verifying adequate luminal closure following an endoluminal procedure.

When a medical procedure (mini-invasive or not) is performed on an organ which needs to show under normal circumstances of functioning a fluidic tightness towards its local environment, one must make sure that no discontinuity, nor any passage or opening is present in the organ wall(s) defining the concerned lumen or cavity.

Medical practice is moving towards less and less invasive approaches to treat diseases and pathologies, especially in surgery. These less invasive procedures advantageously allow for a decreased intra- and post-operative complication rate, a decreased length of stay, a faster return to activity for the patient and less costs for the hospital and the healthcare system.

Laparoscopy has become a standard of care, routinely performed worldwide, whereas more and more interventional procedures are being performed endoscopically, by gaining access to the body of the patient through a natural orifice.

During such procedures, it is also common practice to inject filling gas by means of an insufflator (known per se), which can maintain a determined pressure value of filling gas within a cavity or organ of a patient. As the injection, suction and pressure monitoring of gas can be finely controlled when using such an insufflator, it is possible to maintain a precise internal constant gaseous pressure value.

Such filling gas can in particular be present in the cavity containing the considered organ or adjacent to the latter.

As mentioned before, certain organs in a body need to function in complete fluidic tightness compared to their surroundings. Having content from one of these organs leak into the adjacent organs or body cavity spaces can lead to severe consequences for the subject.

During several widely performed surgical procedures, this fluidic tightness is voluntarily broken (colonic resections, Roux-en-Y gastric Bypass, . . . ). However, physicians can also inadvertently cause unintended leaks by perforating an organ by accident while performing a medical procedure.

The flow of content or material from the considered hollow organ into the adjacent or surrounding space(s) or organ(s) is widely known in the medical community as a «leak». Leaks can appear from anastomosis, staple lines or perforations, to name only a few causes.

Post-operative anastomotic leaks lead to severe complications in patients undergoing surgery, complications range from sepsis, increased cancer recurrence to even death. This increased post-operative complication rate also leads to an important economic burden for the healthcare system.

It is common knowledge that anastomotic leaks occur due to several factors, one of them being incomplete closure of the anastomosis during the operation. Due to the severity of the consequences, several intraoperative «leak testing» methods have been developed and are currently available and commonly used to test the complete closure of the anastomosis (e.g. colored fluids, pressurized air). However, they are not sensitive enough and many failed anastomosis give a negative result to the intraoperative test used.

Having a reliable intraoperative leak test is of great importance because it allows the surgeon to repair the failed anastomosis before finishing the operation, saving possible complications for the patient and increased costs for the hospital.

US 2015/272499 has shown that the use of a test gas can provide a more sensitive and reliable test method than those currently available in the prior art.

As explained in this document, test gas is injected in a controlled manner into the organ and the gas exchange between the organ and the surrounding cavity is monitored and evaluated to establish the potential presence of a leak in the organ.

However, in this US document the organ and the cavity are considered as being perfect containers, whereas the real environment during an intervention is controlled and far from being perfect.

For example, in a not perfect environment, the body cavity itself, in which the considered organ is lodged, is generally subject to leak towards the outside.

In addition, the measurement results are also impacted by the implementation of the measurement and are dependent on the parameters used for realizing said measurement.

To summarize, the measurement environment is in practice not perfect and the process of measuring impacts itself said environment, and thus the reliability of the collected results and data.

So, even if it represents a significant progress over the prior state of the art, the method and system described in this US document still show several shortcomings which prevent any standardization of the measurement, due to a lack of precision and repeatability and are a key impediment to the constitution of an extensive database that could be used for computing the presence and the size of an incomplete closure or leak, and for determining its degree of severity.

Indeed, insufflated gas tends to leak during a surgical procedure involving, for example, a pneumoperitoneum, a factor that is not taken into account by US 2015/272499, nor any other known prior art procedure and that leads to a less precise and not standardizable test.

Furthermore, hollow organs can be open ended or not and they are also typically soft. As a result it is hard to predict the rise of the pressure induced by gas injection at a certain flow. While reaching a target differential pressure value by injecting test gas in the lumen, a luminal pressure safety threshold may be hit or even crossed, as the rise of pressure induced by such an injection is hard to predict. If a luminal pressure safety threshold is reached an obvious solution consists for the system to trigger a safety measure to quickly make the luminal pressure drop (such as opening an exhaust valve or activating suction of the luminal content). This is not desirable as it would stop the measurement, prevent it from being conclusive and the user would then need to restart the experiment.

Moreover, most hollow organs present in the human body have walls that are multi-layered. For example the stomach wall has mucosa, submucosa, muscularis and serosa layers. Different organs also have different wall thicknesses: from a few millimeters for the colon to a centimeter for certain regions of the stomach. For this reason, different organs with similar incomplete closure will have different behaviors when gas is injected within them under similar conditions.

Finally, patients of different BMI and different ages will have both different anatomies, with hollow organs and adjacent cavities of different dimensions and, mostly depending on age and conditions, different compliances. The behavior of hollow organs and cavities of different patients will thus behave differently under similar injection parameters (flow or target injection pressure). For example, in abdominal laparoscopy it is known that for a peritoneal insufflation of 12 mmHg the intraperitoneal volume can range from 2-3 liters for an athletic young male adult, to 8 liters for a post-partum women or a morbidly obese patient.

These anatomical and mechanical differences imply very different behaviors of organs and cavity under similar injection parameters.

It is a main aim of the invention to overcome at least the main previous shortcomings of the prior art mentioned herein before, and as much as possible also taking into account the previously mentioned circumstances and anatomical considerations.

SUMMARY

Therefore, the invention proposes a method for automatically detecting a clinically relevant leak and/or inadequate closure following a medical procedure, in an at least partially hollow organ or mutually fluidly connected hollow organs, residing in the interior volume of a body cavity, said test method comprising the steps of:

injecting, via adapted injection means, a specific test gas or a gas mixture containing at least one test gas, into said organ(s), wherein said test gas is not commonly produced or naturally present within the body of the subject, or is present or produced in a precisely known amount or concentration, analyzing the gas mixture and measuring in particular the concentration of test gas in the interior volume of the body cavity or at least in the space adjacent to said organ(s), and possibly the gas pressure within said volume or space, via adapted detection means and at least during a measurement window, evaluating the likelihood of the presence of a leak or of the existence of a faulty closure, and its degree of severity, by comparing stored data and real-time data with each other, via adapted computational means which also manage said injection and detection means, test method characterized in that the pressure difference between the interior of the hollow organ(s) and its (their) adjacent space or the interior volume of the body cavity is controlled or mastered at least at a given moment during the or at least one measurement window, and in that the pressure difference during the or a measurement window is either set at a predetermined appropriate value, which is set automatically by the computational means based on user input and/or data retrieved from a database, or set by a practitioner, or is controlled so as to follow a predetermined value/time curve by providing a progressive injection of the test gas (TG) or of the gas mixture containing it.

A system allowing to perform this method is also part of the invention.

Thus, the invention provides a method and a system that are able to provide and/or maintain a predetermined or known pressure difference between the hollow organ and the adjacent space at least at a point in time during the measurement window. This is for example done by simultaneously measuring the pressure inside the hollow organ and the adjacent space and creating and maintaining the desired pressure difference between the two, and exploited in the evaluation process allowing to assess the integrity of the organ. Achieving and/or maintaining such a controlled pressure difference allows greater precision and reliability during the gas analyzing and measurement phases.

BRIEF DESCRIPTION OF THE DRAWINGS

The invention will be better understood using the description below, which relates to preferred embodiments, given by way of non-limiting examples and explained with reference to the accompanying drawings, in which.

DETAILED DESCRIPTION

Figure 1:
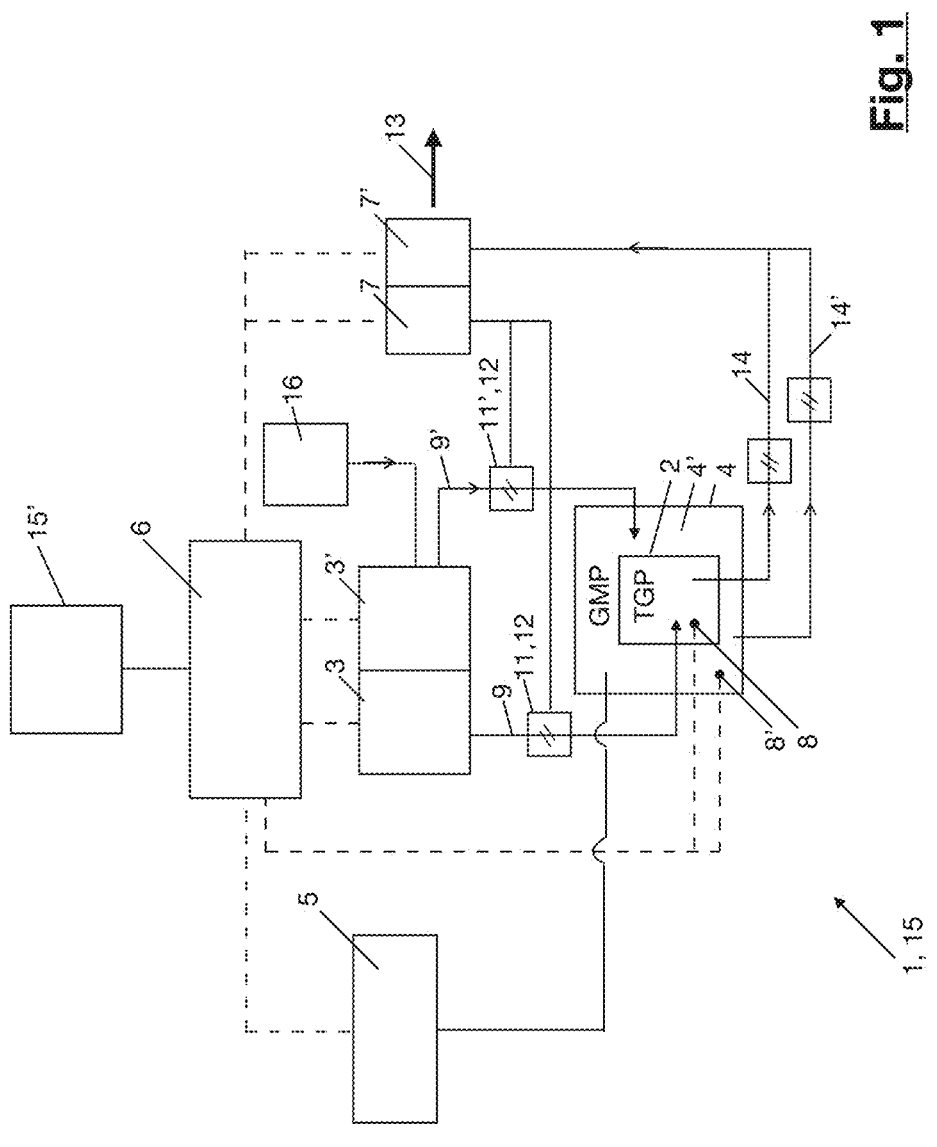
FIG. 1 is a general symbolic and functional representation of a system according to the invention.
Figure 2:
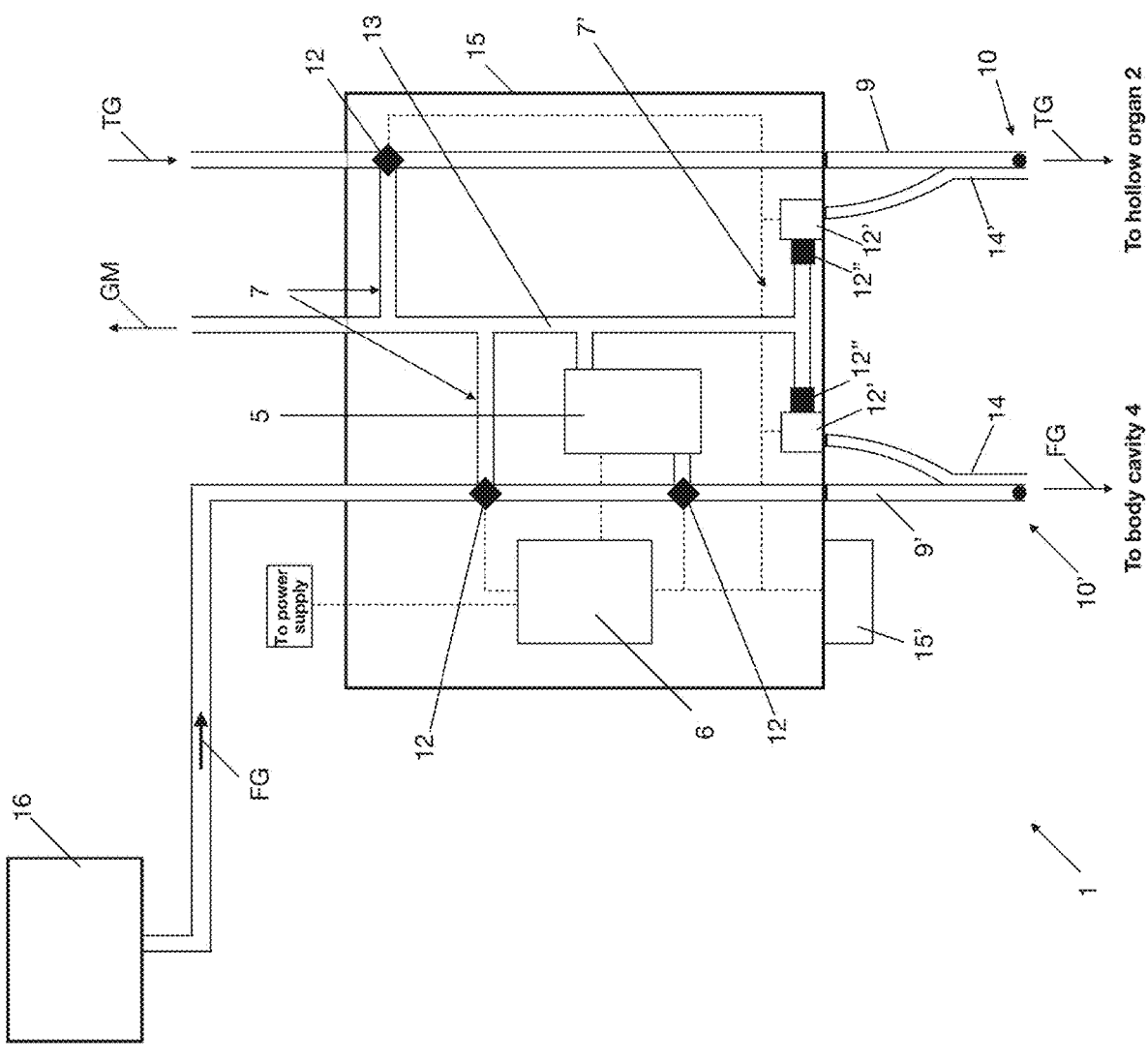
FIGS. 2 to 7 are other symbolic representations of various alternative embodiments of the system according to the invention.

On FIGS. 1 to 7, the continuous or solid lines represent fluidic connections and the dotted or dashed lines represent electrical connection (signal or power).

According to a first aspect, the invention deals with a method for automatically detecting a clinically relevant leak and/or inadequate closure following a medical procedure, in an at least partially hollow organ 2 or at least two mutually fluidly connected hollow organs, residing in the interior volume 4' of a body cavity 4.

Said test method mainly comprises the steps of:

injecting, via adapted injection means 3 a specific test gas TG or a gas mixture containing at least one test gas TG into said organ(s) 2, wherein said test gas TG is not commonly produced or naturally present within the body of the subject (for example $N_2O$), or is present or produced in a precisely known amount or concentration, analyzing the gas mixture GM and measuring in particular the concentration of test gas TG in the interior volume 4' of the body cavity 4 or at least in the space adjacent to said organ(s) 2, and possibly the gas pressure GMP within said volume 4' or space, via adapted detection means 5 and at least during a measurement window, evaluating the likelihood of the presence of a leak or of the existence of a faulty closure, and its degree of severity, by comparing stored data and real-time data with each other, via adapted computational means 6 which also manage said injection and detection means 3 and 5.

According to the invention, the pressure difference $\Delta P$ between the interior of the hollow organ(s) 2 and its (their) adjacent space or the interior volume 4' of the body cavity 4 is controlled or mastered at least at a given moment during the or at least one measurement window, and in that the pressure difference ($\Delta P$) during the or a measurement window is either set at a predetermined appropriate value, which is set automatically by the computational means (6) based on user input and/or data retrieved from a database, or set by a practitioner, or is controlled so as to follow a predetermined value/ time curve by providing a progressive injection of the test gas (TG) or of the gas mixture containing it.

The additional differential pressure control provided by the invention allows to free the test gas concentration measurement from the negative influence of the not perfect measuring environment provided by the body cavity 4. Thus, it is possible to determine precisely said concentration which in turn provides the opportunity to assess reliably and in a standardized manner the integrity of the tested organ 2, and if the case occurs the seriousness of the leak or of the faulty closure, and so its clinical relevance (in particular by comparison with stored reference data acquired previously in similar conditions and circumstances).

The measurement window may include only the (preferably repeated) sampling of the gas mixture GM in the adjacent space or interior volume, or also the consecutive analyzing step(s).

In line with a first possible embodiment of the invention, the pressure difference $\Delta P$ is partly or entirely mastered by controlling the injection of test gas TG into the hollow organ(s) 2, preferably simultaneously monitoring directly or indirectly the test gas pressure TGP in said organ(s) 2 and the gas pressure GMP in said body cavity 4.

To measure the gas pressure inside the organ 2 and around the outside of the organ 2 (volume 4' of the cavity 4), adequate sensors are arranged in said organ 2 and in said cavity 4, or in fluidic circulation lines 9, 9' (tubings) leading to said organ 2 and into said cavity 4, for gas entering or exiting purposes.

In the context of said first embodiment, or alternatively with respect to said embodiment, the pressure difference $\Delta P$ is partly or entirely mastered by controlled injection of filling gas FG, via adapted injection means 3', and/or aspiration of gas mixture GM from within the body cavity 4, via adapted evacuation or suction means 7, 7'. The gas pressure GMP in said cavity 4 is advantageously simultaneously monitored directly or indirectly and the injected filling gas FG is different from the test gas TG.

But preferably the invention provides that the pressure difference $\Delta P$ is mastered by combining a controlled injection of test gas TG into the hollow organ(s) 2 with a controlled injection of filling gas FG into and/or aspiration of gas mixture GM from the interior volume 4' of the body cavity 4.

From the foregoing disclosure and the attached drawings the person skilled in the art understands that the method of the invention for detecting, evaluating and classifying clinically possible leaks or gas permeable closures in organs is performed under the management and supervision of the computational means 6, for example an adequately programmed computer with adapted storage means and communication means.

More specifically, the pressure difference $\Delta P$ is automatically and dynamically controlled by the computational means 6, either i) by monitored injection of test gas TG and/or filling gas FG, or ii) by monitored derivation, before its actual injection, of at least part of the flow of test gas TG intended to be injected into the hollow organ(s) 2 and/or at least part of the flow of filling gas FG intended to be injected into the body cavity 4 and/or iii) by monitored suction of some of the test gas TG present in the hollow organ(s) 2 and/or of some of the gas mixture GM present in the interior volume 4' of the body cavity 4.

To perform the various tasks in the context of the inventive method, the computational means 6 must be provided with real-time relevant measurement data (pressures and gas compositions—the latter from the detection module 5).

To that end, the gas pressures TGP, GMP in the hollow organ(s) 2 and in the body cavity 4 are measured by respective sensors 8, 8' linked to the computational means 6 and located either somewhere along the gas feeding lines 9, 9' provided for the injection of the test gas TG and of the filling gas FG, or preferably at the exit tips 9, 9' of said lines 8, 8' situated within the hollow organ(s) 2 and the body cavity 4 respectively.

Of course, the pressure values which prevail in the organ 2 and in the body cavity 4 will be dependent on the types of said organ and cavity, the nature of the previous intervention, the clinical condition and the physiological status of the concerned body part and of the patient, etc.

According to one aspect of the invention, the pressure difference $\Delta P$ may be maintained constant at least during the measurement window, advantageously at a set value.

In accordance with an advantageous feature of the invention in this context, the set value of the pressure difference $\Delta P$ used during the or a measurement window may be an optimized value, advantageously depending at least on the type of the concerned hollow organ 2, on the type of medical procedure previously performed and/or on the size and/or the number of the aperture (s) forming the leak, and possibly on the planned duration of a detection cycle, said set value of the pressure difference $\Delta P$ being preferably at least equal or superior to a determined minimal value and at the most equal or inferior to a determined maximal value (for example set by the practitioner, preprogrammed and/or resulting from previous similar procedures).

Hence, the set value of the pressure difference $\Delta P$ during the measurement window is a predetermined appropriate value, which is set automatically by the computational means 6 based on user input and/or data retrieved from the database, or set by a practitioner.

More precisely, said optimized value of the pressure difference $\Delta P$ used during the or a measurement window is determined automatically in the course of or after a detection cycle based on the gas mixture pressure (GMP) variation and/or on the measured test gas TG concentration data, preferably determined during or after a previous or first operative detection or measurement cycle and then stored in the database, by performing a continuous or stepwise increase of said pressure difference $\Delta P$ and a monitoring of the concentration of test gas T in the interior volume 4' of the body cavity 4.

According to another aspect of the invention, the pressure difference $\Delta P$ follows a predetermined value/time curve resulting from a progressive injection of test gas TG, said predetermined value/time curve being selected by the computational means 6 depending at least on the type of the concerned hollow organ 2 and on the type of medical procedure previously performed and based on stored data or parameters resulting from previous leak detection procedures.

Thus, with respect to this second aspect and as a safety precaution, it may be advantageously envisaged that the pressure TGP of test gas TG in the hollow organ(s) 2 is increased stepwise, by advantageously providing predetermined waiting times (settling periods) at each of the successive pressure levels.

For example, in the course of stepwise increase injection, the pressure difference ΔP is kept stable at different values during a waiting time. During a waiting time, the computational means can evaluate, based on the pressure monitoring in the adjacent space, whether the current pressure difference ΔP value reveals the presence of an incomplete closure.

If it does reveal the presence of an incomplete closure, it can evaluate, by comparing the pressure evolution in the adjacent space with stored data, whether the current pressure difference value is adequate.

If the current pressure value difference is adequate, the computational means may monitor or control the pressure difference value to equal the current pressure difference value for a longer time (until a conclusive result is reached).

If the current pressure value difference is inadequate, the computational means monitor or control the pressure difference value to the next step increase following the predefined pattern.

Based on the measurement of the pressure (as a result of the progressive injection) in the adjacent space, the computational means identifies a desirable ΔP value when it is reached.

If the user chooses to repeat the detecting operation cycle, the computational means will select the previously identified ideal ΔP value as the ΔP value for the detecting operation cycle that is about to start.

Furthermore, the inventors have discovered that ideal or optimized ΔP values for different possible sizes of holes exist. For a given opening size, this optimized ΔP value is considered ideal because it is above the value at which the test gas will leak through a considered opening in the hollow organ and below the value at which an excessive amount of test gas leaks through said opening. An excessive amount is problematic firstly because it may put the patient at risk and secondly because when the pressure GMP in the adjacent cavity approaches a safety threshold, to ensure patient safety, some of the gas mixture present in the adjacent cavity needs to be immediately evacuated (through active suction or by triggering opening of an exhaust valve). This emergency evacuation interrupts the controlled measurement, and thus the leak detection cycle, which needs to be restarted again: this is an important limitation.

The ideal ΔP value for a specific opening size is the value that both ensures patient safety and avoids the necessity to restart the experiment with different parameters.

Moreover, and as mentioned above, the detection of smaller incomplete closures will take more time than bigger holes because the test gas will take more time to diffuse through. This implies that at certain ΔP values, the measurement will be conclusive but will take a significant amount of time. In these specific cases, there exists a higher ΔP value at which the measurement would also be conclusive but would take significantly less time.

Because of the reasons outlined above, a most desirable or optimized ΔP value can be determined for each hole or leak size, which ensures that the measurement will be safe, conclusive and efficient timewise.

The following alternatives or additional features may also be considered in relation to the method, possibly in partial mutual combination with each other:

the pressure difference (ΔP) may be managed by combining a controlled injection of test gas (TG) into the hollow organ(s) (2) with a controlled injection of filling gas (FG) into and/or aspiration of gas mixture (GM) from the interior volume (4') of the body cavity (4);

the pressure (GMP) of the gas mixture (GM) in the interior volume (4') of the body cavity (4) may be adjusted to an appropriate value, advantageously a selected stored value or a value resulting from a previous leak detection cycle, before injecting filling gas (FG) into said volume (4') and thus before injecting test gas (TG) into the hollow organ (2);

a leak detection cycle may comprise progressively injecting test gas (TG) into the hollow organ (2), determining an optimized value of the pressure difference (ΔP) and exploiting said value to continue and complete said cycle;

a leak detection cycle may comprise progressively injecting test gas (TG) into the hollow organ (2), determining the presence or not of more than one leaking aperture and exploiting this information to continue and complete said cycle.

According to an advantageous embodiment, the method may consist in performing a first leak detection cycle based on the progressive injection of test gas (TG) followed by at least one other, preferably only a second, leak detection cycle, advantageously based on a set predetermined appropriate value of the pressure difference (ΔP), preferably determined during the first leak detection cycle.

From the previous exposed features and embodiments, the person skilled in the art will have realized that the method of the invention may be practically implemented according to numerous alternatives, in particular as far as the control or the mastering of the pressure difference ΔP is concerned.

Figure 8:
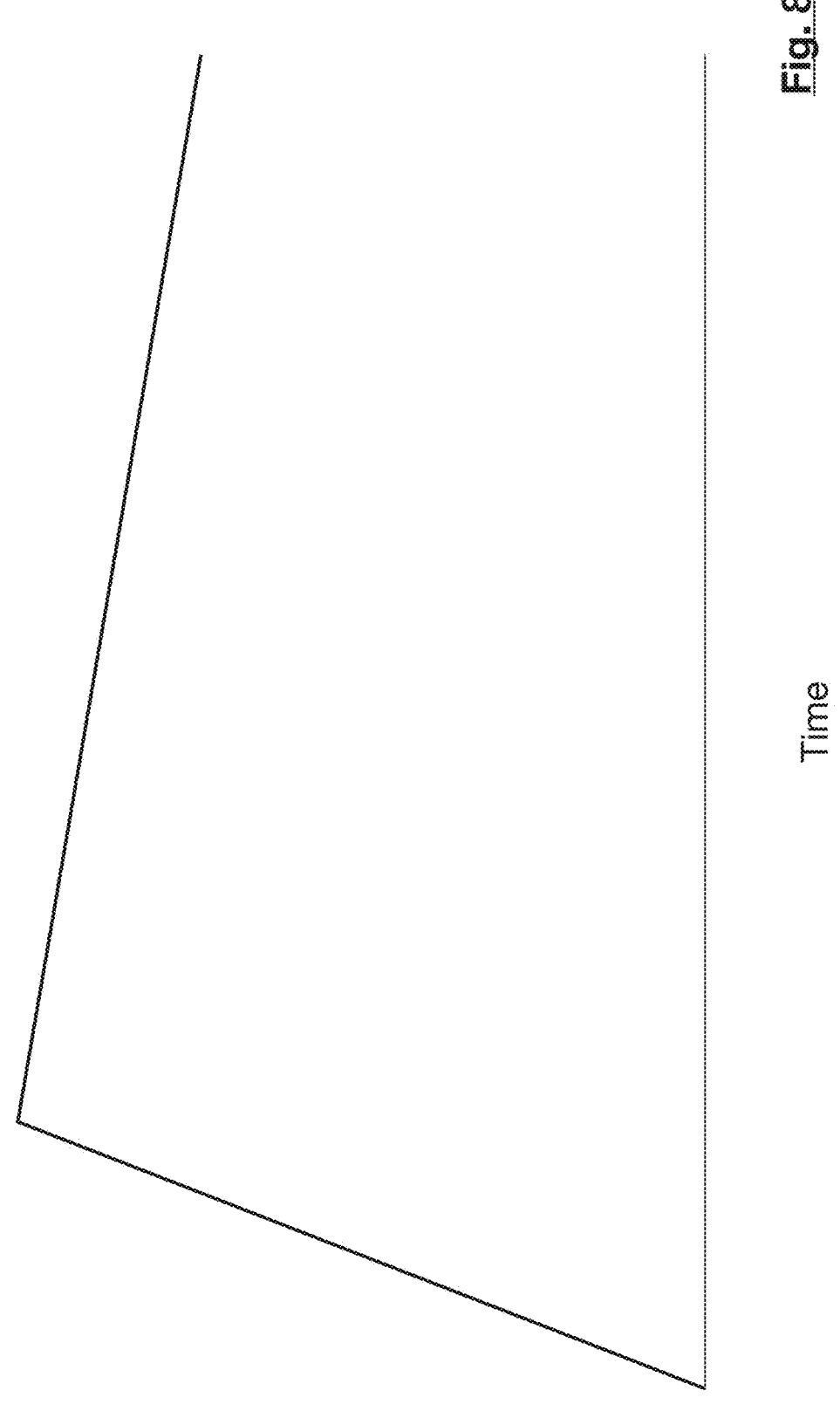
FIG. 8 is a time curve of the profile of the pressure difference between the inside of the hollow organ to be tested and the surrounding space outside said organ, when applying the detection method of the invention making use of the system shown in any of FIGS. 2 and 3.

In a first alternative, the method may comprise measuring the pressure GMP in the body cavity 4 (set previously by the physician) through an adapted and adequately arranged sensor 8', and control the injection of test gas TG to achieve the desired pressure difference ΔP between the organ 2 to be tested and the adjacent space/cavity 4 at a moment in time at least during the measurement window (see FIG. 8).

In a second alternative, the method may comprise measuring the pressure GMP in the body cavity 4 and adjusting it automatically to the most appropriate pressure for the test, then control the injection of test gas TG to obtain the desired pressure difference ΔP at a given moment at least during the measurement window (see FIG. 8).

This second alternative is especially relevant in the case, described later, in which the system integrates a surgical insufflator (laparoscopic for example). Decreasing the GMP pressure allows for a detection cycle to be completed at given ΔP value, and thus to lower the absolute GMP value, thereby reducing the risk of the GMP reaching a safety threshold causing the problem and limitations previously described.

It is then beneficial for the detection cycle to start at the lowest GMP value possible.

The first alternative improves on the prior art by measuring the pressure GMP in the body cavity 4, which allows to take into account insufflation or filling gas FG leaking out of the body cavity 4 when treating the measurement data, running the calculations and evaluating the situation and thus to achieve a higher precision during the test. The second alternative can, in addition, set the most appropriate pressures for the test improving resolution and minimizing the risk of an unclear test.

Figure 9:
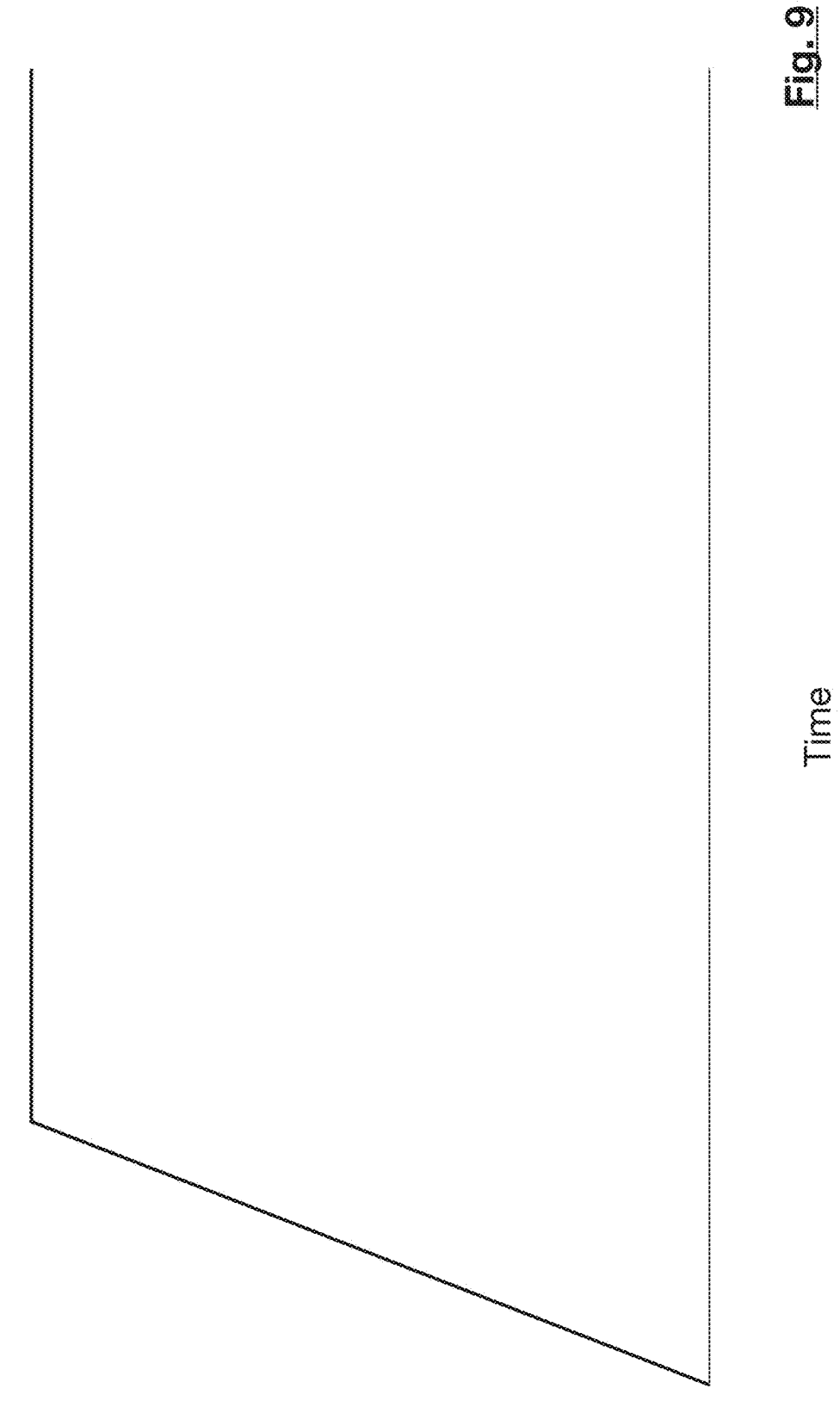
FIG. 9 is a time curve of the profile of the pressure difference between the inside of the hollow organ to be tested and the surrounding space outside said organ, when applying the detection method of the invention making use of the system shown in any of FIGS. 5 and 6, and, FIG. 10 shows experimental time curves representing the concentration of test gas in the cavity of an air tight compliant housing in which an ex-vivo hollow organ having a 1 mm hole and injected with test gas, is placed.

In a third alternative, the method may comprise measuring the pressure GMP in the body cavity 4 (set by the practitioner) through a sensor 8', and control the injection of test gas TG to achieve the desired pressure difference ΔP between the organ 2 to be tested and the adjacent body cavity 4 and maintain its value through the duration of the test by repeatedly measuring the pressure TGP in the organ 2 to be tested through a pressure sensor 8 present at the distal tip 10 of the injection line or tube 9 and repeatedly adjusting the injection of test gas TG accordingly (see FIG. 9).

In a fourth alternative, the method may comprise measuring the pressure GMP in the body cavity 4 and adjusting it to the most appropriate pressure for the test, then control the injection of test gas TG to obtain the desired pressure difference ΔP and maintain it through the duration of the test by repeatedly measuring the pressure TGP in the organ 2 through a pressure sensor 8 present at the distal tip 10 of the injection tube 9 and repeatedly adjusting the injection of test gas TG accordingly (FIG. 9).

The third alternative improves on the prior art by, in addition to measuring the pressure in the body cavity 4, maintaining the desired pressure difference ΔP for the duration of the test by a controlled injection of test gas TG. This is of great benefit for the detection of smaller incomplete closures, for which the gas may take more time to diffuse and pass through the hole(s) or aperture(s) in the organ 2 to the body cavity 4. Hence, maintaining a constant pressure difference ΔP throughout the experiment will accomplish such need. The fourth alternative can, in addition, set the most appropriate pressures for the test and maintain them, improving resolution and minimizing the risk of an unclear test.

In a fifth alternative, the method may comprise measuring the pressure in the body cavity 4, set by a physician, and injecting test gas TG in order to achieve the desired pressure difference ΔP between the organ 2 to be tested and the adjacent space 4'/cavity 4 and maintaining it through the duration of the leak test (or at least during the measurement phase of said test) by repeatedly measuring the pressures TGP, GMP in the organ 2 and body cavity 4 and aspirating or insufflating filling gas FG (i.e. $CO_2$) in the body cavity 4 accordingly.

In a sixth alternative, the method may comprise measuring the pressure GMP in the body cavity 4 and adjusting it to the most appropriate pressure for the test, then injecting test gas TG into the organ 2 to obtain the desired pressure difference ΔP and maintaining it through the duration of the test (or at least during the measurement phase of said test) by repeatedly measuring the pressure TGP in the organ 2 and the pressure GMP in the body cavity 4 and aspirating or insufflating filling gas FG (i.e. $CO_2$) in the body cavity 4 accordingly.

The fifth alternative improves on the prior art by, in addition to measuring the pressure in the body cavity 4, maintaining the desired pressure difference ΔP for the duration of the test (or at least during the measurement phase of said test) by aspirating and/or insufflating the body cavity 4. This is of great benefit for the detection of smaller incomplete closures, for which the test gas TG may take more time to diffuse and pass through the hole(s) or aperture(s) in the organ(s) 2 to the body cavity 4. Hence, maintaining a constant pressure difference ΔP throughout the experiment will accomplish such need. The sixth alternative can, in addition, set the most appropriate pressure for the test and maintain it, improving resolution and minimizing the chances of an unclear test.

All of the abovementioned alternative methods preferably allow for the pressure difference ΔP during the or a measurement window to be controlled so as to follow a predetermined value/time curve by providing a progressive injection of the test gas TG or of the gas mixture containing it. Said curve may be specific and adapted to the considered organ or/and to the previously realized surgical procedure. According to a beneficial embodiment, the method according to the invention may allow for the test gas pressure TGP to increase in the organ 2 to be tested in a stepwise manner, by increasing to a certain percentage (i.e. 20%) of a set, optimal or maximum value and maintaining that pressure for a given amount of time until another percent increase (i.e. 40%) and continuing this procedure until achieving the desired pressure difference ΔP between the body cavity 4 and the organ 2 to be tested. This stepwise increase may be adapted for different organs, which will in turn increase the precision of the test of said organs.

In order to increase even further the level of accuracy and the degree of reliability of the method of the invention, its constitutive sequence of operational steps may be repeated at least once, or even several times.

Thus, the method may consist in performing at least two successive operating detection cycles, each one comprising the considered respective injection, analysis and evaluation steps and at least one measurement window. A discharge step wherein the hollow organ(s) 2 is (are) substantially emptied of at least the test gas TG, and preferably substantially emptied of all gases, is inserted between two successive detection cycles.

Of course the test gas TG can be injected as pure (i.e. single component) gas and may be a specific regulatory clinical gas, such as N2O.

Nevertheless, and according to a beneficial embodiment of the invention, the test gas is injected as part of a gas mixture and preferably said injected gas mixture is ambient air, preferably filtered and sterilized, the used test gas TG being one of its gaseous components, for example $O_2$ or $N_2$.

One way to control at least partly the pressure in the hollow organ 2 and/or the pressure difference ΔP by controlled aspiration of the interior of said hollow organ 2.

The following complementary description and additional explanations can be taken into consideration when contemplating the features and alternatives of the method according to the invention.

For the reasons outlined above, it is beneficial that the computational means control dynamically the pressure difference and also advantageously making it vary during the detection. Such a variation can be done following for example a progressive increase or a stepwise increase.

Thus, the pressure difference value ΔP can change throughout the measurement: for example following a progressive injection or a specific time curve which is set by the computational means based on user input and/or data retrieved or set by the practitioner.

For the reason outlined above, parameters of the organs being tested can be discovered during a progressive or stepwise increase. Especially the volume, compliance and presence of a hole can be identified or made more precise.

It may happen that multiple incomplete closures are present in an organ to be tested. It is likely that those holes will not be identical in size or behavior with respect to a given pressure difference. As mentioned earlier, different holes sizes have different ideal ΔP values and at a given ΔP value, a larger hole may let a significant TG flow through, while a smaller one may just not let any gas through.

The method is adapted to identify the presence of multiple incomplete closures by analyzing the pressure (and potentially TG concentration) measured in the adjacent cavity.

As described in greater details above and below, progressive injection curves can be useful to learn about the characteristics of the organ to be tested and the presence of one or multiple holes and, in each case, to identify the ideal pressure difference ΔP value to carry a dedicated measurement cycle allowing to confirm the presence of the incomplete closure and evaluate the likelihood of the presence of the leak and potentially its degree of severity.

For example, the system carrying out the inventive detection method may perform a first detection cycle with a ΔP following a progressive injection curve. The computational means can evaluate based on the pressure (and potentially TG concentration) monitoring in the adjacent space, whether one or multiple incomplete closure are present in the hollow organ being tested, the computational means further identifying the best suited delta P value associated to each of the said one or multiple incomplete closure(s) identified.

This system may then successively:

output an information to the user informing him that the presence of one or multiple leaks is suspected, complete a discharge step where the hollow organ is emptied for its TG content, and potentially where the adjacent cavity is emptied and filled with FG up to a desired pressure value, complete a new detection cycle using the Delta P value identified during the previous detection cycle completed with Delta P values following a progressive injection curve, potentially complete yet another detection cycle with another ideal Delta P value previously identified.

In the course of progressive increase injection, the pressure difference ΔP value is progressively increased, and thus the dynamic control may involve stopping the progressive increase at one pressure value that is appearing adequate for the detection and maintaining the pressure difference at that adequate value for some time.

Also, in the course of stepwise increased injection, the pressure difference is kept stable at different values during a waiting time, and the dynamic control may involve stopping the stepwise increase at one of the steps that is appearing adequate for the detection ongoing.

Hereinafter, several practical aspects and issues relating to the detection method, mainly based on conclusions of the inventors after experimental results, will be explained in more details hereinafter in relation to practical preferred embodiments of the invention.

In the context of the invention, a known maximum safe insufflation pressure for adjacent cavities exists. Exposing patients to excessive pressure leads to a variety of complications and comorbidities that are well documented for common technical approaches such as laparoscopy and thoracoscopy.

For example, in abdominal laparoscopic surgery, surgeons operate by setting a pneumoperitoneum with an FG injection target pressure typically between 10 and 15 mmHg, depending on the patient characteristics. Most commercially available surgical insufflator systems allow surgeons to set a target pressure for cavity insufflation (typically 12 mmHg), but also to set a maximum pressure threshold that should not been exceeded in the cavity (typically 15 mmHg). Depending on surgical insufflators systems, once the threshold is reached it will start an alarm and stop insufflation, with more advanced system automatically lowering the pressure, typically by a valve opening (passive or active).

In a favored embodiment, the detection method is based on analysis of the GM sampled from one single point in the adjacent cavity. In the laparoscopic case for example, the GM will be sampled from a surgical access port in the adjacent cavity wall. If the cavity is peritoneum, the cavity is typically 2 to 6 liters large depending on the patient and the insufflating pressure. In any case, if during a leak detection performed according to the inventive method only a few cc of TG mixture are leaking through an incomplete closure of the tested organ into the adjacent cavity, it will likely go undetected or generate an irregular signal. The TG detection signal may be irregular because circulation and mixing of gas is uncontrolled. Because the detection method is based on measuring the TG concentration, a TG irregular signal does not allow the detection to be conclusive.

The inventors have observed, in the course of their experiments, that it is necessary that at least 10% of the adjacent cavity be filled with TG (or TG mixture) to reach a consistent and standardized measurement.

It is also an objective of the claimed method and system to allow a detection within a time range that is acceptable for users/practitioners and compatible with operating room uses.

This leads to the fact that, given certain features and properties of incomplete closures, the system would best work at a special pressure difference ΔP that creates a flow that allows the adjacent cavity to be filled with at least 10% TG in less than a minute.

The optimized pressure difference ΔP mentioned will be greatly different in value depending on the incomplete closure dimensions which can vary from a few millimeters to a few centimeters, but also on its shape which can sometimes be approximated by a slit and sometimes by a "hole". Obviously the characteristics of the hole or otherwise shaped incomplete closure is unknown at the initiation of a leak detection.

In order to provide a leak detection according to the invention that would be desirable for clinicians, a minimal value of ΔP should be used.

Of course the flows and pressure variations behaviors and the pressure difference values will be different when considering different types of adjacent cavities.

As described above the detection method is based on the measurement of TG leaking out of the hollow organ through an incomplete closure and later sampled at a distant point in the cavity. For this very principle to work in practice, it is necessary that enough FG (filling gas) has been injected in the adjacent cavity before the TG (test gas) injection starts so that organs are well spaced apart from one other. The organ spacing ensures that the incomplete closure is not clogged by neighboring tissue and is in free fluidic communication with the cavity created by FG injection: this allowing TG to freely leak through. If not enough FG is injected, the incomplete closure may stay plugged by adjacent tissue, or a pocket of TG may stay trapped below tissue and would not be detected.

Using again the example of abdominal laparoscopic surgery, surgeons typically consider that a full organ separation is reached from a 10 mmHg peritoneal insufflation.

The inventors observed, during controlled testing, that 7 mmHg is an efficient value for the adjacent cavity insufflation pressure at the beginning of a detection cycle. If an incomplete closure is present, during TG injection in the organ to be tested, TG mixture will leak into the adjacent cavity thereby increasing the GMP pressure. If the GMP pressure reaches the maximum safety pressure mentioned above, typically 15 mmHg, the injection of TG in the organ will need to be stopped thereby interrupting the detection process. Of course for certain injection parameters—TG flow and target organ pressure—depending on the size of the incomplete closure, the injection could create an unexpected and very quick pressure rise in the cavity which could be dangerous for the patient.

Figure 10:
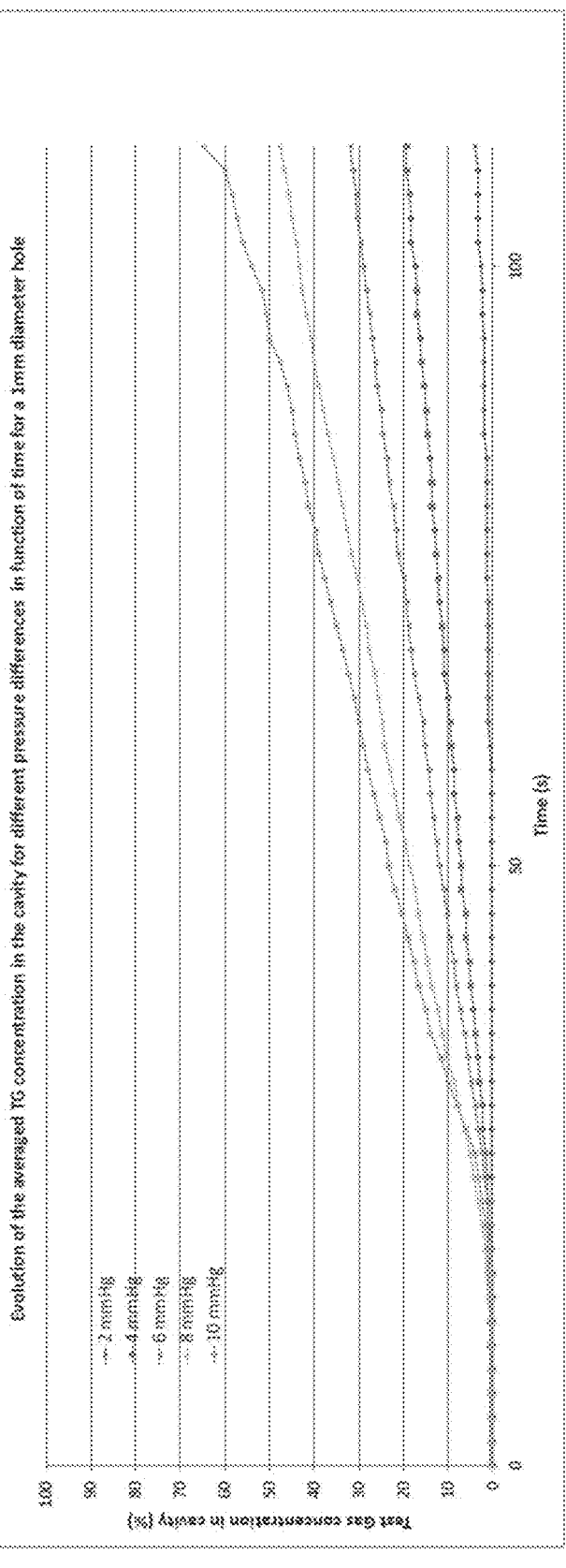

The previous comments will be better understood by considering the graph of FIG. 10.

FIG. 10 depicts the results of controlled experiments where a 1 mm hole is created in an ex-vivo organ which is then placed within an air tight compliant housing. Following the invention detection method, TG is then injected in a controlled manner in the organ and the GM is simultaneously sampled from the housing (cavity), and the concentration of TG is measured. The concentration of TG in the adjacent cavity is plotted as a function a time for different pressure differences providing the curves of FIG. 10.

As can be observed on FIG. 10, to ensure that a 10% concentration of TG is measured in the housing in less than a minute for a 1 mm hole, a minimum pressure difference $\Delta P$ of 6 mmHg should be used. This illustrates the fact that, for a certain configuration of organ, cavity and hole characteristics, there is a minimal $\Delta P$ value for which the detection would be conclusive in an acceptable timeframe.

As described above the pressure values will depend on the type of organs and cavity, the nature of the intervention and the patient and organ clinical conditions and physiological status. Some of this information is known before the start of the leak detection procedure and will be used by the system computational means to identify and set the most appropriate $\Delta P$ value.

Advantageously, based on this patient and procedure information, the system computational means will also identify and set the most appropriate adjacent cavity FG pressure value before initiating the leak detection cycle.

However, the rate of leakage of TG in the adjacent cavity will be greatly dependent on parameters that are unknown when the detection is initiated.

Firstly the exact characteristics of the patient anatomy and of the organ are generally unknown: the volume of the organ and its compliance are mostly only statistically deduced.

Secondly, and most importantly, the characteristics of the incomplete closure, hole, slit, aperture or other gas leaking opening are unknown: its position, size and shape are unknown.

Considering again the example given on FIG. 10, using the same injection parameter, that is a 6 mmHg pressure difference $\Delta P$, for the same organ and cavity, but with a 10 mm incomplete closure, would almost instantly cause the pressure to surpass the safety pressure threshold and potentially hurt the patient.

The inventors have observed in a controlled setting during ex vivo experiments that you needed a 4 times greater $\Delta P$ value between a 1 mm hole and a 8 mm hole to achieve 10% of TG volume within the adjacent cavity in less than a minute for the exact same organ and setting (position and shape of the incomplete closure, cavity volume).

Those examples illustrate the fact that, for certain patient and procedure characteristics, a same $\Delta P$ cannot be used to ensure a safe and fast leak detection. It implies that, in this schematic example, there is probably not a single appropriate value of the pressure difference that could be predetermined by the system that would allow a fast and conclusive detection for incomplete closures between 1 and 10 mm in the organ model of the experiment above.

An optimized value for $\Delta P$ is one that allows a quick and conclusive leak detection in agreement with defined measurement parameters targets: that is when the measurement completed at the optimized $\Delta P$ value allows a defined minimum TG concentration threshold to be reached in the cavity in less than a defined maximum detection timing.

An optimized value of the pressure difference $\Delta P$ can only be determined by the computational means of the system during or after a first operative detection performed with a continuous or stepwise increase of the pressure difference. The determination of the optimized value of the pressure difference $\Delta P$ can be determined based on the evolution of the pressure GMP and/or concentration of TG measurement in the body cavity, as mentioned before.

The computational means of the system will identify if an optimized $\Delta P$ value is reached by evaluating whether the evolution of the pressure GMP and/or of the TG concentration at a given pressure difference value is sufficient to complete a measurement complying with measurement parameter targets.

In a first possible practical embodiment of the invention, a first leak detection cycle is completed following an appropriate [$\Delta P$ value vs time] curve selected by the system, and the evolution of the pressure GMP and/or of the TG concentration is (are) analyzed by the computational means to identify an optimized pressure difference $\Delta P$ value. The gaseous contents of the organ and of the cavity are then purged, to lower the TG concentration. Next injection of FG can be performed in the organ cavity to reach an appropriate pressure GMP.

Subsequently a second leak detection cycle is performed using the previously identified optimized pressure difference value as the appropriate value set by the system.

In a second practical embodiment of the invention, a leak detection cycle is initiated following a [$\Delta P$ value-time curve] deemed appropriate by the computational means based on the data entered by the user or retrieved from a database. This value/time curve may, for example, be a step function according to which $\Delta P$ is increasing in steps of 2 mmHg starting with a 1 mmHg value. As the injection of TG in the organ starts, so does the analysis of the TG concentration in the adjacent organ cavity. The computational means analyze the evolution of the TG concentration in the adjacent cavity and/or the pressure GMP to identify if and when an optimized $\Delta P$ value is reached.

As mentioned above, an optimized value for $\Delta P$ is one that allows a quick and conclusive leak detection which relies on an appropriate flow of TG through the leak. A flow will be considered appropriate when it allows a defined minimum TG concentration threshold to be reached in the cavity in less than a defined maximum detection timing. The flow through the incomplete closure can be readily evaluated from the TG concentration in the cavity and/or the pressure GMP evolution.

In the course of the $\Delta P$ increase, the computational means of the system can then identify when an optimized $\Delta P$ value is reached as the first/lowest $\Delta P$ value from which the flow through the leak reaches the appropriate flow value.

When such an optimized $\Delta P$ value is identified, the computational means will stop the $\Delta P$ value increase to keep the detection cycle occurring at the identified optimized $\Delta P$ value.

In other words, the computational means will stop the pressure increase when the flow through the incomplete closure is sufficient for a fast and conclusive leak detection.

As will be understood, an optimized $\Delta P$ value (or value range) depends greatly on parameters such as position and size of the incomplete closure, and cannot be derived before the injection starts. Leak detection carried without an optimized ΔP value may lead to non-conclusive detections, lengthy detection cycle or safety related interruptions necessitating the measurement to be started over.

The method, and the associated system described in more detail hereunder, allow in a preferred embodiment of the invention to circumvent this limitation by providing a way to identify and adapt in the course of the measurement an optimized ΔP value ensuring a safe, fast and conclusive leak detection cycle.

The present invention also encompasses specifically, as shown in FIG. 1 and in FIGS. 2 to 7 by way of various illustrative embodiments and alternatives, a system 1 for automatically detecting a clinically relevant leak and/or inadequate closure following a medical procedure, in an at least partially hollow organ 2 or mutually fluidly connected hollow organs, residing in the interior volume 4' of a body cavity 4. Said system 1 comprises at least:

injection means 3 designed for controlled injection of a specific test gas TG, or a gas mixture containing at least one test gas TG, into said organ(s) 2, said injection means 3 comprising or being associated with first gas pressure measuring means 8, detection means 5 designed for analyzing the gas mixture GM and in particular measuring the concentration of test gas TG, in the interior volume 4' of the body cavity 4 or at least in the space adjacent to said organ(s) 2, and possibly the gas pressure GMP within said volume 4' or space, and computational means 6 designed for managing the injection and detection means 3 and 5, for storing and retrieving data from an integrated local or remote database and for analyzing data and evaluating the likelihood of the presence of a leak or of the existence of a faulty closure, and its degree of severity, by comparing stored and real-time data.

According to the invention, the computational means 6 are linked to sensor means 8, 8' allowing to determine the pressure difference ΔP between the interior of the hollow organ(s) 2 and the adjacent space or interior volume 4' of the body cavity 4, said computational means 6 controlling or mastering said pressure difference ΔP by driving accordingly associated injection and/or suction means 3, 3', 7, 7', incorporating said test gas TG injection means 3.

Thus, the system 1 is designed, configured and adapted to be able to carry out the method described herein before, i.e. at least some of the previous alternatives of said method.

According to a first and simplest embodiment, the system 1 may master the pressure difference ΔP only by controlling the test gas TG injection means 3, and thus by acting only on the test gas TG pressure in the organ 2.

Nevertheless, the system 1 advantageously comprises, in addition to the test gas TG injection means 3, also filling gas FG injection means 3' designed for injecting in a controlled manner a filling gas FG into the interior volume 4' of the body cavity 4.

Hence, said system 1 may set the most appropriate pressure GMP in the body cavity 4, by bypassing and/or by diverging the filling gas FG insufflation flow, and may adjust and measure the injection of test gas TG in order to achieve the desired pressure difference ΔP between the organ 2 to be tested and the adjacent space/cavity 4 at a moment in time at least during the measurement window.

Alternatively, the system 1 may comprise a surgical insufflator 16 and set the most appropriate pressure in the body cavity 4 and then adjust and measure the injection of test gas TG in order to achieve the desired pressure difference ΔP between the organ 2 to be tested and the adjacent space/cavity 4 at that moment in time at least during the measurement window.

The pressure sensors 8, 8' may be arranged and situated in various ways.

Figure 5:
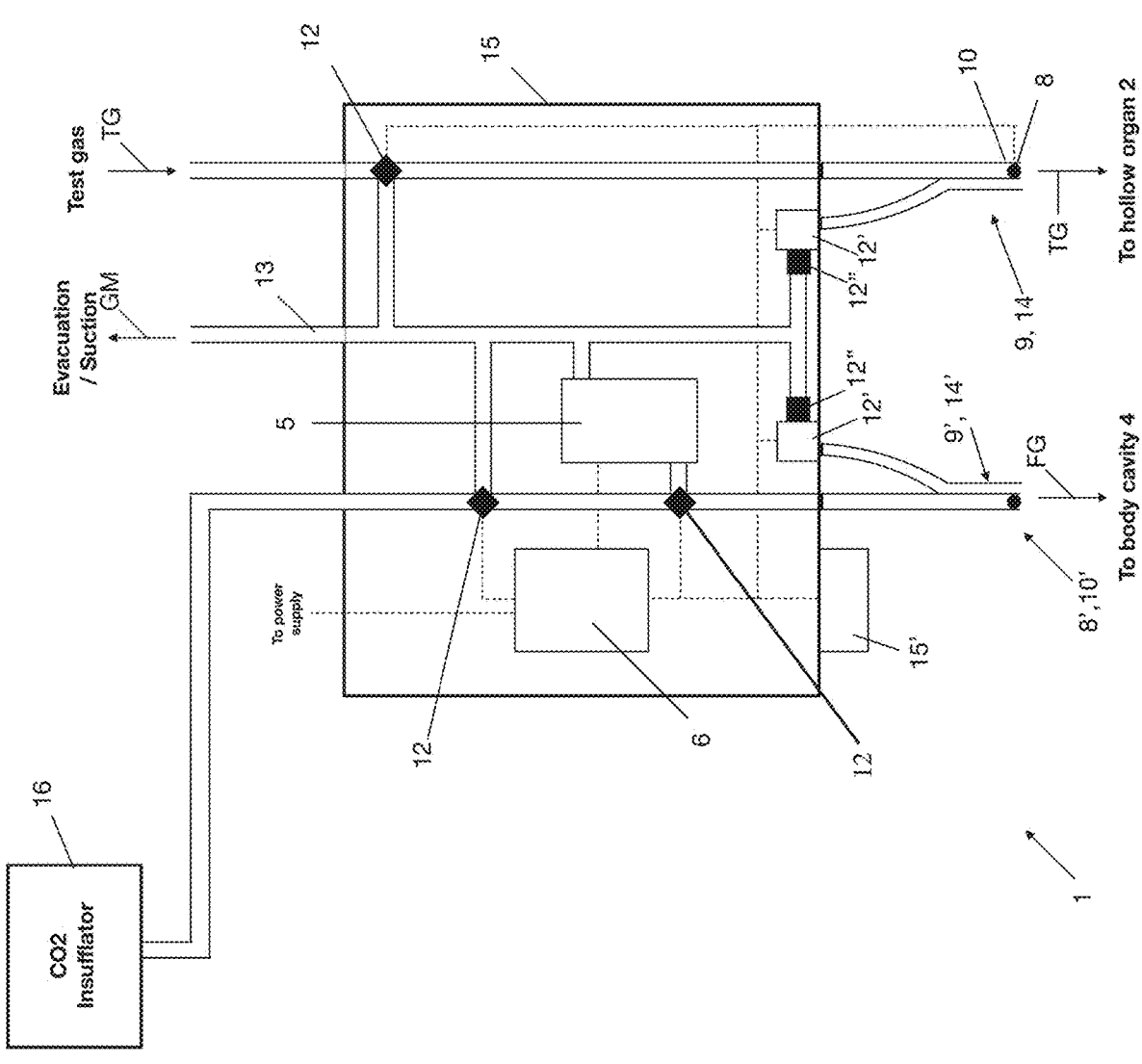
Figure 6:
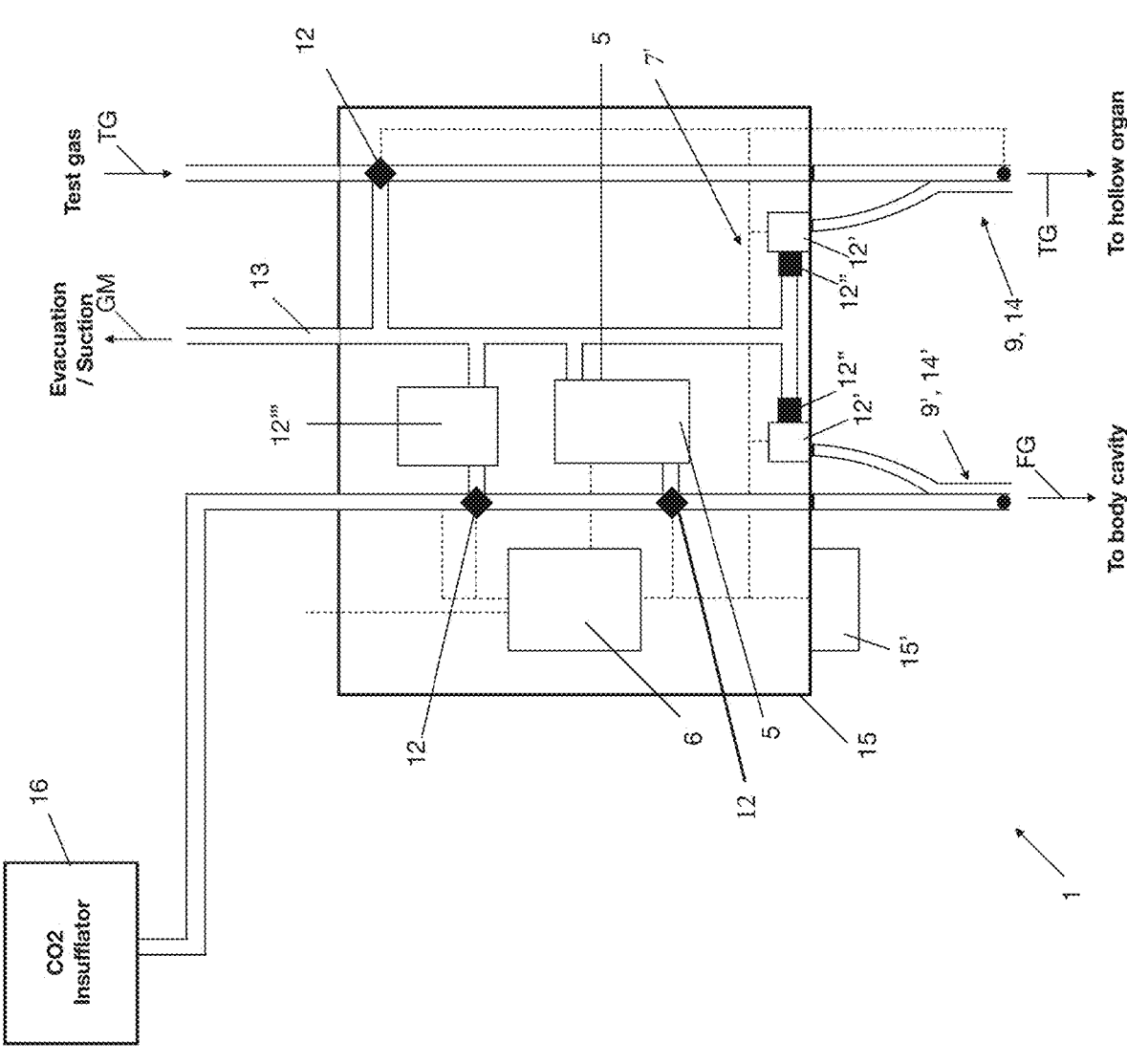
Figure 7:
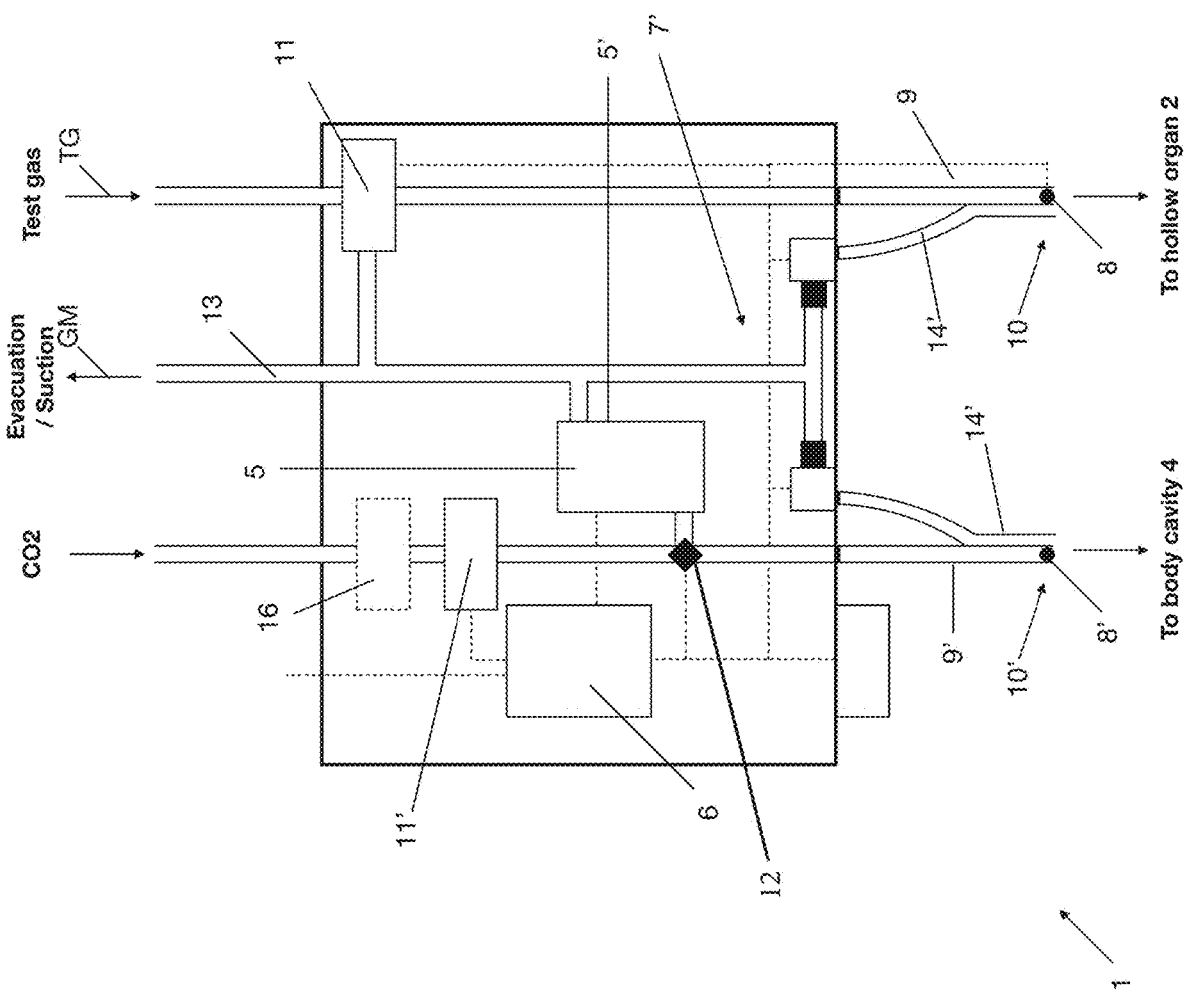

In accordance with a preferred feature of the invention, shown in particular in FIGS. 5 to 7, each of the gas feeding lines 9, 9' being part of one of the test gas TG and filling gas FG injection means 3 and 3' respectively, comprises or is associated with a pressure sensor 8, 8', preferably located at or near the exit tip 10, 10' of the considered line 9, 9'.

In this case, it may be envisaged that the system 1 measures the pressure in the body cavity 4 through a pressure sensor 8' present at the tip 10' of the line or tubing 9' connecting the system 1 with the subject, set by the physician, and adjusts and measures the injection of test gas TG in order to achieve the desired pressure difference ΔP between the organ 2 to be tested and the adjacent space/cavity 4 and maintains it through the duration of the leak test (or at least during the measurement phase) by repeatedly measuring the pressure in the organ 2 through another pressure sensor 8 present at the distal tip 10 of the test gas TG injection tube or line 9 and repeatedly adjusting the injection of test gas TG accordingly (see FIG. 5).

It can also be envisaged that the system 1 measures and sets the most appropriate pressure in the body cavity 4 through a sensor 8' present at the tip 10' of the tubing or line 9' connecting the system 1 with the subject, by bypassing and/or by diverging the insufflation flow of filling gas FG, and adjusts and measures the injection of test gas TG in order to achieve the desired pressure difference ΔP between the organ 2 to be tested and the adjacent space/cavity 4 and maintains it through the duration of the leak test (or at least during the measurement phase) by repeatedly measuring the pressure in the organ 2 through a pressure sensor 8 present at the distal tip 10 of the injection tube or line 9 and repeatedly adjusting the injection of test gas TG accordingly (see FIGS. 2, 3, 5 and 7).

Alternatively, the sensor means 8, 8', which are associated with the test gas TG and filling gas FG injection means 3, 3', are located within the unit 15.

Advantageously, the system 1 also comprises a surgical insufflator 16, i.e. a separate external insufflator or an integrated internal insufflator, which measures and sets the most appropriate pressure in the body cavity 4 and is used by the system 1 to help achieving the pressure difference ΔP control (in addition to the TG injections means).

Figure 4:
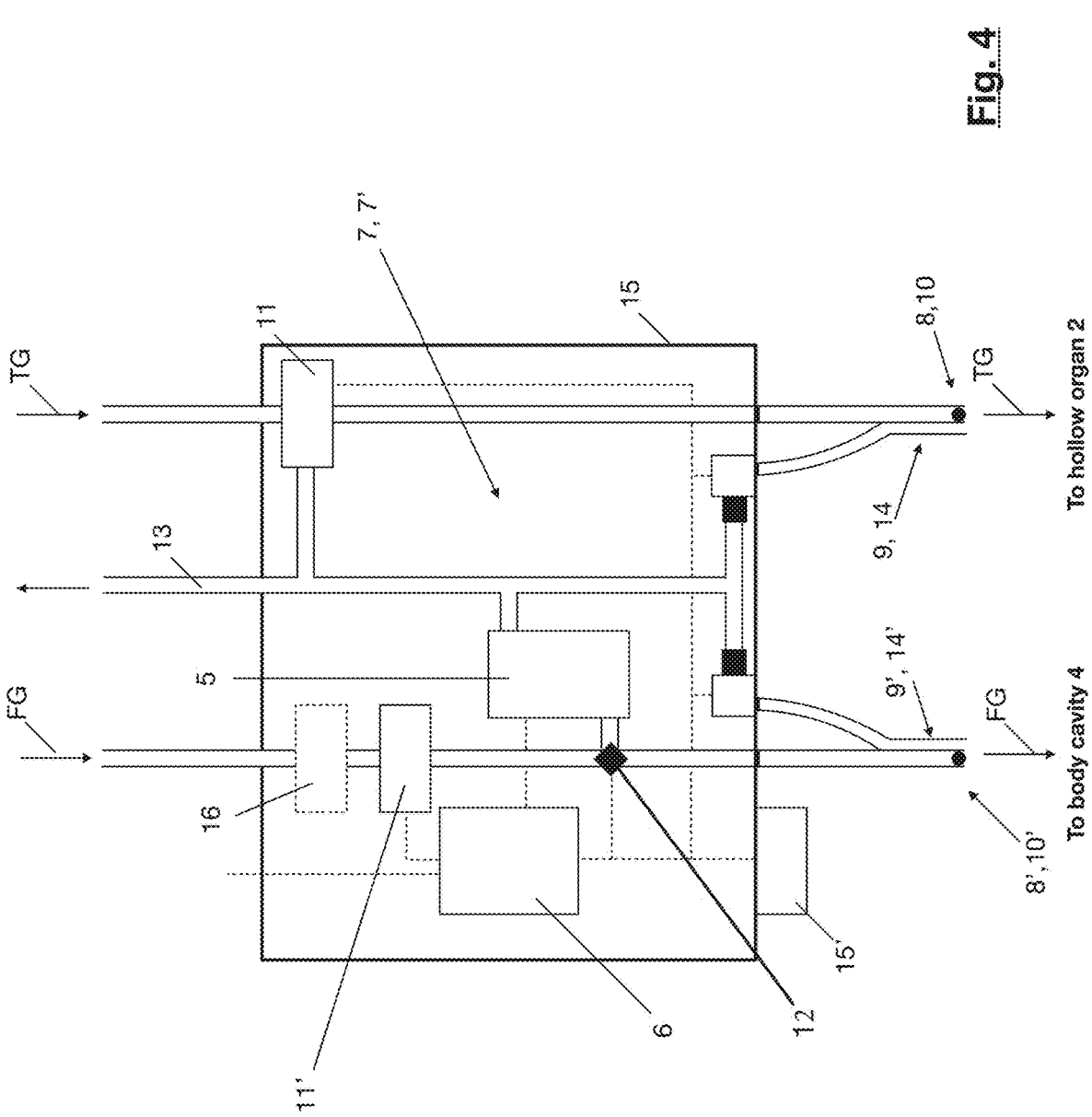

According to another embodiment, shown in FIG. 4, each of the gas feeding lines 9, 9' being part of one of the test gas TG and filling gas FG injection means 3 and 3' respectively, may comprise corresponding volume and flow control means 11 and 11'.

As shown on FIGS. 1 to 3 and 5 to 7, the system 1 may alternatively incorporate, in order to control both the test gas TG and the filling gas FG injections, gas evacuation means 7 designed for limiting, for example by controlled derivation of a part of the flow in the gas feeding lines 9, 9', the quantity of test gas TG injected into to the hollow organ(s) 2 and/or the quantity of filling gas FG injected into the body cavity 4.

Alternately or in addition to said gas evacuation means 7, the system 1 may also comprise gas suction means 7' designed to perform a controlled sucking of test gas TG from the hollow organ(s) 2 and/or gas mixture GM from the body cavity 4, at or near the exit tips 10, 10' of the gas feeding lines 9, 9'.

As shown in FIGS. 2, 3 and 5 to 7, the gas evacuation and gas suction means 7 and 7' comprise valves 12, 12' controlled by the computational means 6, said valves including derivation valves 12 designed and configured to selectively link the gas feeding lines 9, 9' to a main collective evacuation and suction duct 13, and suction valves 12' designed and configured to selectively link specific suction line portions 14, 14' to said main collective duct 13, an overpressure valve 12" being advantageously associated to each suction valve 12'.

As shown on FIGS. 2 to 7, an additional valve 12 may be arranged to control the fluidic connection between the gas feeding line 9' (delivering the filling gas FG) and the entrance of the detection means 5 (for example a combination of pumps and gas analyzer known per se). In particular, said valve 12 can be of use when the detection means 5 are to be isolated from the FG gas stream if no detection is requested.

In a preferred embodiment, said system 1 comprises injection, insufflation, evacuation and aspiration capabilities for both the organ of interest 2 and the body cavity 4. The system 1 decides, after pressure measurements, if the results lay between its confidence intervals by comparison with results stored in its local or remote database, and repeats the measure if needed, after aspirating some of the test gas TG from the organ 2 to be tested and/or some of the gas mixture GM from the adjacent body cavity 4 (see FIG. 7).

All of the embodiments and alternative construction of the system 1 may perform the test gas pressure increase in the organ to be tested in a stepwise manner, by increasing to a certain percentage (i.e. 20%) and maintaining that pressure for a given amount of time until another percent increase (i.e. 40%) and continue until achieving the desired pressure difference ΔP between the body cavity 4 and the organ(s) 2 to be tested. This stepwise increase can be adapted for different organs, which will in turn increase the precision of the test of said organ(s) 2.

Figure 3:
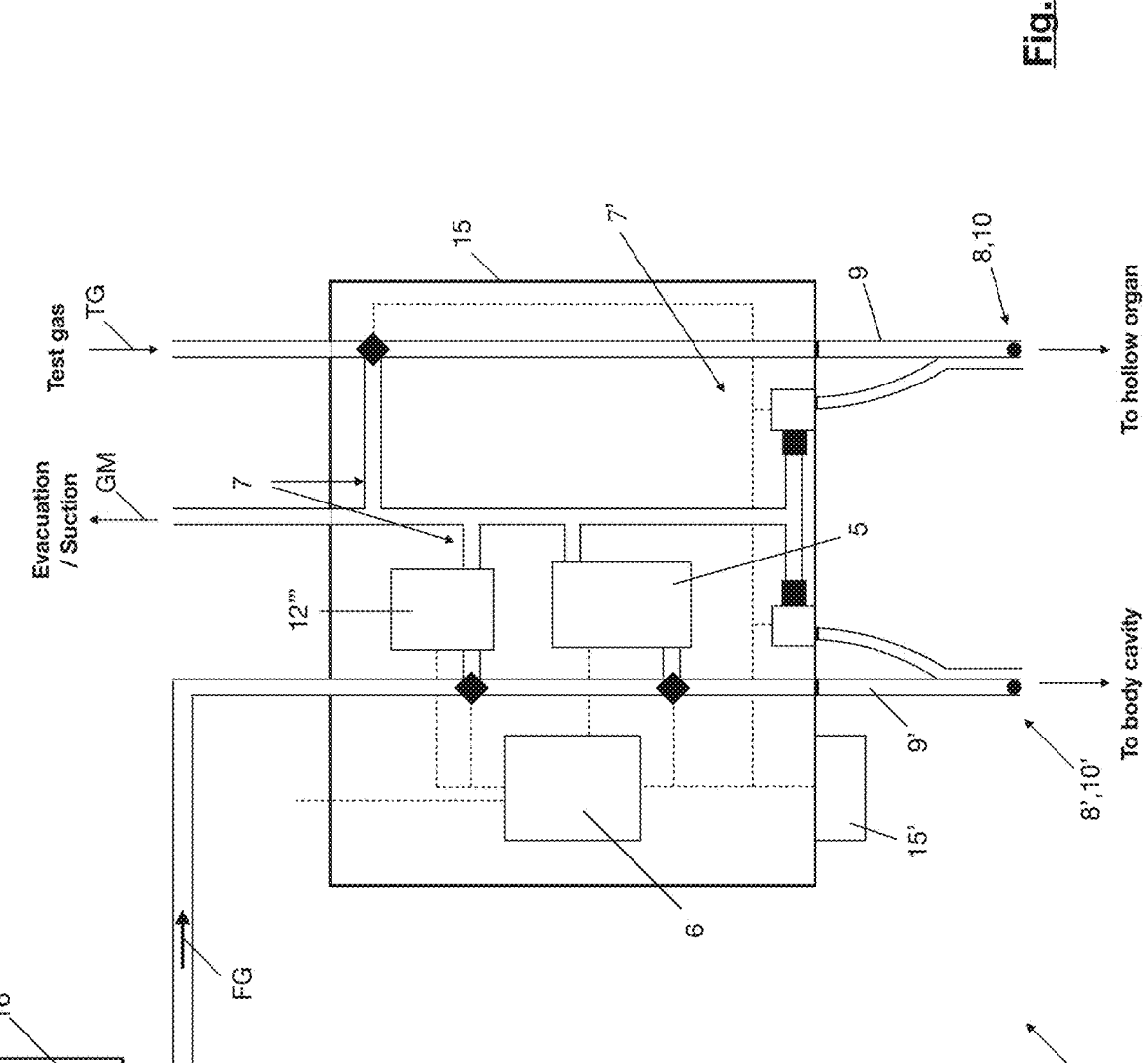

According to another feature of the invention, the system 1 may also comprise a pressure chamber 12''' linking the filling gas FG feeding line 9', connected to an insufflator 16, with the main collective duct 13 and containing a control valve which is configured to be intermittently opened to avoid flow alarms coming from said insufflator (see FIGS. 3 and 6).

Depending on the considered previously described embodiment or alternative, the system 1 according to the invention shows the following improvements over the prior art:

adding a means to measure the pressure in the body cavity 4, which allows to take into account gas leaking out of the body cavity 4 when measuring and running the calculations and achieve a higher precision during the test;

setting the most appropriate pressure for the test, improving resolution and minimizing the chances of an unclear test. The most appropriate body cavity pressures and pressure differences may be different for different types of procedures or organs, the system 1 can take that into account based on data retrieved from the local or remote database;

adding means to maintain the desired pressure difference ΔP for the duration of the test by a controlled injection of test gas TG and/or by aspirating and/or insufflating the body cavity 4. This is necessary or at least beneficial for the detection of smaller incomplete closures, for which the gas may take more time to diffuse and pass through the hole to the body cavity.

Preferably, all of the main operative components of the system 1, including at least part of the injection means 3, 3', the detection means 5, the computational means 6, the volume and flow control means 11, 11' and the various valves 12, 12', 12", 12''', are comprised within a physical and functional unit 15, preferably equipped with a user interface 15'.

This unit 15 may be connected at least to a power source and to sources of test gas TG and filling gas FG.

The test gas TG source may be an external insufflator 16, as shown on FIGS. 2, 3, 5 and 6.

Nevertheless, the invention may also provide that the system comprises a laparoscopic or surgical insufflator 16 fitted within the physical and functional unit 15 (FIGS. 4 and 7).

Of course, the person skilled in the art will understand that the system according to the invention is configured and comprises all operative and functional means necessary to perform the test method, including one, two or several detection cycles, as described herein before.

More specifically, at least part of its operative and functional means 3, 5, 6, 7, 7', 8, 8', 11, 11' are configured to perform, for example under the control of a management software, or an expert or trained AI software, the various method steps and alternatives set forth.

Of course, the invention is not limited to the embodiments described and represented in the accompanying drawings. Modifications remain possible, particularly from the viewpoint of the composition of the various elements or by substitution of technical equivalents without thereby exceeding the field of protection of the invention.

The invention claimed is:

1. A method for automatically detecting a clinically relevant leak and/or inadequate closure following a medical procedure, in an at least partially hollow organ or mutually fluidly connected hollow organs, residing in an interior volume of a body cavity, said method comprising the steps of:

injecting, via adapted injection means a test gas or gases containing at least one test gas, into said hollow organ(s), wherein the test gas or the at least one test gas is not commonly produced or naturally present within the body cavity, or is present or produced in a precisely known amount or concentration, analyzing and measuring a concentration of the test gas or the at least one test gas and a pressure of a gas mixture in the interior volume of the body cavity or at least in a space adjacent to said hollow organ(s), via adapted detection means and at least during a measurement window, evaluating a likelihood of a presence of the clinically relevant leak or the inadequate closure, and a degree of severity the clinically relevant leak or the inadequate closure, by comparing stored data and real-time data with each other, via adapted computational means which also manage said injection and detection means, wherein a continuous increase of the concentration of the test gas or the at least one test gas in the gas mixture in the interior volume of the body cavity or at least in the space adjacent to said hollow organ(s) indicates a relevant leak and/or inadequate closure, wherein:

a pressure difference between the hollow organ(s) and either the space adjacent to the hollow organ(s) or the interior volume of the body cavity is controlled at least at a given moment during the measurement window, the pressure difference during the measurement window is
    (i) set at a predetermined value, which is set automatically by the computational means based on user input and/or data retrieved from a database, (ii) set by a practitioner, or (iii) controlled so as to follow a predetermined value/time curve by providing a progressive injection of the test gas or of the gas mixture containing the at least one test gas.

2. The method according to claim 1, wherein the pressure difference is partly or entirely by controlling the injection of the test gas or the gases containing the at least one test gas, into the hollow organ(s), and simultaneously monitoring directly or indirectly the pressure of the test gas or the gases containing the at least one test gas in said hollow organ(s) and the pressure of the gas mixture in said body cavity.

3. The method according to claim 1, wherein the pressure difference is partly or entirely by controlled injection of a filling gas, via the adapted injection means, and/or aspiration of the gas mixture from the body cavity, via adapted evacuation or suction means, the pressure of the gas mixture in said body cavity being simultaneously monitored directly or indirectly and the injected filling gas being different from the test gas or the gases containing the at least one test gas, wherein both a continuous increase of the concentration of the test gas or the at least one test gas in the gas mixture in the interior volume of the body cavity or at least in the space adjacent to said hollow organ(s) and a decrease in an amount of the filling gas indicate a relevant leak and/or inadequate closure.

4. The method according to claim 1, wherein the pressure difference is by combining a controlled injection of the test gas or the gases containing the at least one test gas into the hollow organ(s) with a controlled injection of a filling gas into and/or aspiration of the gas mixture from the interior volume of the body cavity.

5. The method according to claim 1, wherein the pressure difference is automatically and dynamically controlled by the computational means, either
    i) by monitored injection of the test gas or the gases containing the at least one test gas and/or a filling gas, or
    ii) by monitored derivation, before its actual injection, of at least part of a flow of the test gas or the gases containing the at least one test gas intended to be injected into the hollow organ(s) and/or at least part of a flow of the filling gas intended to be injected into the body cavity, and/or
    iii) by monitored suction of some of the test gas or the gases containing the at least one test gas present in the hollow organ(s) and/or of some of the gas mixture present in the interior volume of the body cavity.

6. The method according to claim 1, wherein the pressure of the test gas or the gases containing the at least one test gas in the hollow organ(s) and the pressure of the gas mixture in the body cavity are measured by respective sensors linked to the computational means and located either somewhere along gas feeding lines provided for the injection of the test gas or the gases containing the at least one test gas and of a filling gas, or at exit tips of said lines situated within the hollow organ(s) and the body cavity respectively.

7. The method according to claim 1, wherein the pressure difference is maintained constant during the measurement window at a set value.

8. The method according to claim 1, wherein a set value of the pressure difference used during the measurement window is an optimized value, depending at least on a type of the concerned hollow organ(s), on a type of medical procedure previously performed and/or on a size and/or a number of the aperture(s) forming the leak.

9. The method according to claim 8, wherein said optimized value of the pressure difference used during the or a measurement window is determined automatically in a course of or after a detection cycle based on pressure variation of the gas mixture in the interior volume of the body cavity and/or on the measured test gas or the at least one test gas concentration data, determined during or after a previous or first operative detection or measurement cycle and then stored in the database, by performing a continuous or stepwise increase of said pressure difference and a monitoring of the concentration of test gas or the at least on test gas in the interior volume of the body cavity.

10. The method according to claim 1, wherein the pressure difference follows a predetermined value/time curve resulting from the progressive injection of the test gas or the gases containing the at least one test gas, said predetermined value/time curve being selected by the computational means depending at least on a type of the concerned hollow organ(s) and on a type of medical procedure previously performed and based on stored data or parameters resulting from previous leak detection procedures.

11. The method according to claim 1, wherein the pressure of test gas or the gases containing the at least one test gas in the hollow organ(s) is increased stepwise, and predetermined waiting times are provided at each of a successive pressure level.

12. The method according to claim 1, wherein the pressure difference is managed by combining a controlled injection of the test gas or the gases containing the at least one test gas into the hollow organ(s) with a controlled injection of a filling gas into and/or aspiration of the gas mixture from the interior volume of the body cavity.

13. The method according to claim 1, wherein the pressure of the gas mixture in the interior volume of the body cavity is adjusted to a selected stored value or a value resulting from a previous leak detection cycle, before injecting a filling gas into said volume and thus before injecting the test gas or the gases containing the at least one test gas into the hollow organ.

14. The method according to claim 1, wherein a leak detection cycle comprises progressively injecting the test gas or the gases containing the at least one test gas into the hollow organ, determining an optimized value of the pressure difference and exploiting said optimized value to continue and complete said cycle, or to perform a consecutive cycle.

15. The method according to claim 1, wherein a leak detection cycle comprises progressively injecting the test gas or the gases containing the at least one test gas into the hollow organ, determining a presence or not more than one leaking aperture and exploiting this information to continue and complete said cycle.

16. The method according to claim 1, wherein the method comprises performing a first leak detection cycle based on the progressive injection of the test gas or the gases containing the at least one test gas followed by at least one other, leak detection cycle, based on the set predetermined value of the pressure difference determined during the first leak detection cycle.

17. The method according to claim 1, wherein the method comprises performing at least two successive operative detection cycles, each one comprising a considered respective injection, analysis and evaluation steps and the measurement window, and a discharge step wherein the hollow organ(s) is (are) substantially emptied of at least the test gas or the gases containing the at least one test gas, and substantially emptied of all gases, is inserted between two successive detection cycles.

18. The method according to claim 1, wherein the method comprises controlling at least partly the pressure in the hollow organ and/or the pressure difference by controlled aspiration of the interior volume of the body cavity.

19. The method according to claim 1, wherein the injected gases containing the at least one test gas is ambient air, filtered and sterilized, the at least one test gas being $O_2$ or $N_2$.

\* \* \* \* \*